United States Patent [19]

Cambron et al.

[11] Patent Number: 4,722,344
[45] Date of Patent: Feb. 2, 1988

[54] RADIOPAQUE POLYURETHANES AND CATHETERS FORMED THEREFROM

[75] Inventors: Ronald E. Cambron, Palm Harbor, Fla.; Donald J. Dempsey, Newbury; Kevin M. Mills, Burlington, both of Mass.; Hartley A. Silverwood, Durham, N.H.

[73] Assignee: Critikon, Inc., Tampa, Fla.

[21] Appl. No.: 866,606

[22] Filed: May 23, 1986

[51] Int. Cl.⁴ .............................................. A61B 6/00
[52] U.S. Cl. .................................. 128/658; 604/265; 604/280
[58] Field of Search ............... 604/265, 280; 128/658; 524/44, 83

[56] References Cited

U.S. PATENT DOCUMENTS

| | | | |
|---|---|---|---|
| 2,212,334 | 8/1940 | Wallerich | 18/58 |
| 2,857,915 | 10/1958 | Sheridan | 128/349 |
| 3,180,883 | 4/1965 | Cast | 528/44 |
| 3,336,918 | 8/1967 | Jeckel | 128/2.05 |
| 3,437,680 | 4/1969 | Farrusey et al. | 528/44 |
| 3,529,633 | 9/1970 | Vaillancourt | 138/118 |
| 3,605,750 | 9/1971 | Sheridan et al. | 128/348 |
| 3,608,555 | 9/1971 | Greyson | 128/348 |
| 3,618,614 | 11/1971 | Fyynn | 128/348 |
| 3,645,955 | 2/1972 | Flynn | 604/280 |
| 3,749,134 | 7/1973 | Slingluff et al. | 604/280 |
| 3,901,829 | 8/1975 | Slingluff et al. | 252/478 |
| 3,907,722 | 9/1975 | Papa et al. | 528/85 |
| 3,939,124 | 2/1976 | DiBella et al. | 528/44 |
| 4,027,659 | 6/1977 | Slingluff | 128/2 M |
| 4,105,732 | 8/1978 | Slingluff | 264/104 |
| 4,156,067 | 5/1979 | Gould | 604/280 |
| 4,182,787 | 1/1980 | Gossens et al. | 428/36 |
| 4,282,876 | 8/1981 | Flynn | 604/280 |
| 4,526,906 | 7/1985 | Wegner | 528/55 |
| 4,581,390 | 4/1986 | Flynn | 604/280 |

*Primary Examiner*—John D. Yasko
*Attorney, Agent, or Firm*—Hamilton, Brook, Smith & Reynolds

[57] ABSTRACT

Catheters formed from polyurethanes containing sufficient halogenated moieties in the polymer structure to make the polyurethanes radiopaque are disclosed. Such polyurethanes can be prepared by employing halogenated diols and/or halogenated diisocyanate reactants. In preferred cases, the catheters are optically transparent in addition to being radiopaque.

26 Claims, 3 Drawing Figures

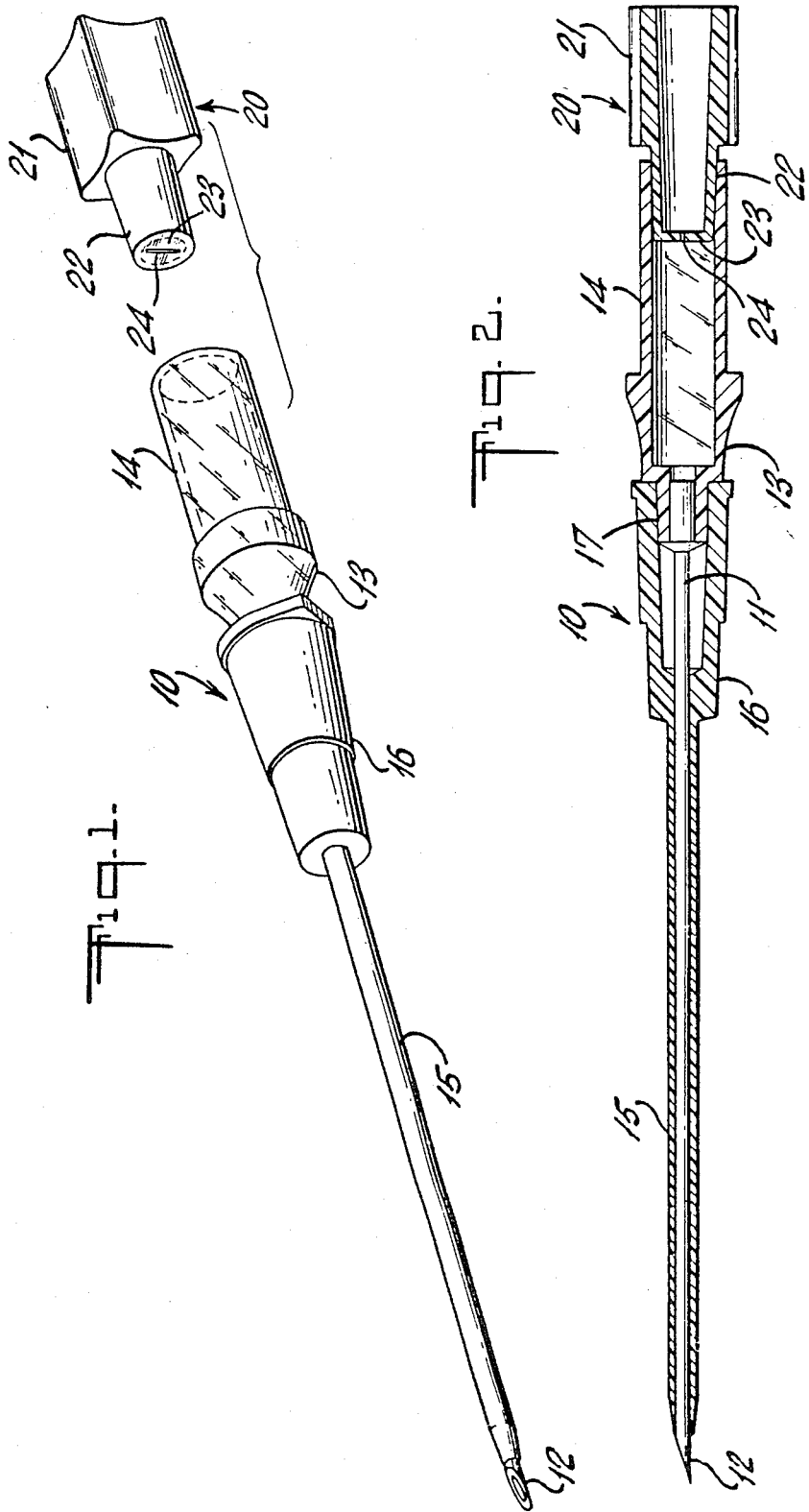

RADIOPAQUE POLYURETHANES AND CATHETERS FORMED THEREFROM

BACKGROUND OF THE INVENTION

Catheters are slender tubes widely employed in the medical field for insertion into body passages, vessels or cavities. They are employed for passing fluids, draining fluids, making examinations, etc.

It is generally desirable that catheters be radiopaque because it is often necessary to determine the precise location of a catheter within its host by X-ray examination. In addition, it would be advantageous if catheters were optically transparent so that the flow of fluids therethrough could be observed.

There has been extensive research over a long period to improve the properties of catheters, including the properties of X-ray opacity and optical transparency. This research is documented, for example, in the patent literature.

U.S. Pat. No. 2,212,334 issued to Wallerich in 1940 describes early attempts to produce an optically transparent catheter having some radiopaque properties. In this patent, Wallerich describes the extrusion of a plastic cellulose material through a tubular molding die coupled with forcible injection of small quantities of X-ray opaque material at uniform brief intervals to vary the X-ray opacity of the extruded catheter at regular intervals.

U.S. Pat. No. 2,857,915 issued to Sheridan describes efforts to produce catheters which were normally transparent to visible light but having an integral continuous opaque stripe running along the length of the catheter. The polymers suggested by Sheridan included nylon, polyester, polyethylene, and vinyl.

The art of adding a radiopaque stripe to a catheter was further refined as described in U.S. Pat. Nos. 4,027,659 and 4,105,732 issued to Slingluff. Slingluff added a highly conductive material, as well as a radiopaque material, to the stripe running along the length of the catheter. Thus, the stripe could be employed for observing the catheter's location with x-rays and for electrically grounding the catheter to allow discharge of any electrostatic charges built up during use of the catheter.

In U.S. Pat. No. 3,605,750, issued to Sheridan et al., catheters having radiopaque distal end portions are described. These are made X-ray opaque by fusing a plastic annulus containing X-ray opaque pigment onto a preformed catheter tube.

U.S. Pat. No. 3,529,633 issued to Vaillancourt describes the many prior efforts to provide a catheter which was optically transparent and yet had radiopaque properties. In this patent, Vaillancourt suggests that catheters be formed from fluorinated polymers, such as polytetrafluoroethylene, having an adequate quantity of precipitated barium sulfate to provide X-ray opacity with a minor portion of the catheter or "window" remaining clear and transparent.

Greyson, in U.S. Pat. No. 3,608,555, suggests incorporating an X-ray opaque substance having an index of refraction close to that of the polymer to provide radiopacity with sufficient optical permeability to permit viewing of fluids within the catheter. Greyson also suggests that crystallization should be minimized for crystalline-forming polymers, such as perfluorocarbon resins.

In U.S. Pat. No. 3,618,614, Flynn suggests multiwall surgical tubing having an inner relatively thick transparent tube encased in a relatively thin, visually transparent, outer shell containing a radiopaque material. Thus, X-rays pass through the lateral edges of the composite tube through a relatively long path at the side edges of the tubing while the central portion remains substantially transparent.

Flynn suggests the addition of certain radiopaque plasticizers to vinyl resins employed in the formation of medical-surgical tubing in U.S. Pat. No. 3,645,955. These plasticizers include halogenated benzoates, such as alkyl 2,5-diiodobenzoates, alkyl or alkoxyalkyl 2,3,4,6-tetraiodobenzoates, or mixtures thereof.

In U.S. Pat. No. 3,336,918, Jeckel describes the use of polyurethane coatings containing radiopaque metal powders such as tin, lead and bismuth, for use in catheters. It had previously been found that the addition of such radiopaque metals accelerated the urethane reaction limiting the pot-life thereof. The specific invention described by Jeckel in this patent is the use of small amounts of diglycolic acid to control or halt the catalytic action of the heavy metal powder on the urethane reaction thereby lengthening the pot-life.

In U.S. Pat. Nos. 3,749,134 and 3,901,829, Slingluff describes yet further attempts to produce catheters which are optically transparent and radiopaque. In these patents, Slingluff suggests blending a small amount of a diol of tetrabromophthalic anhydride and a plasticizer with the thermoplastic resin employed in forming the catheter. The diol is distributed throughout the entire wall of the tubing rendering it radiopaque or, alternately, the diol can be limited to certain areas or zones or added in any desired pattern. The use of such diols and plasticizers is suggested with a wide variety of thermoplastic resins, such as polyethylene, vinyl polymers, nylon, flexible polyurethane, etc.

Goossens et al. suggest that optically clear radiopaque catheters can be formed from certain terpolymers in U.S. Pat. No. 4,182,787. These are terpolymers of polycarbonatepolydiorganosiloxane having carbonate, halocarbonate and polydiorganosiloxane constituents.

U.S. Pat. No. 4,282,876 issued to Flynn describes still another polymer composition intended to produce a combination of optical clarity with radiopacity for catheters. The polymers described are polyurethane resins, alone, or combined with vinyl resins, and having alkyl or alkoxyalkyl 2,5-diiodobenzoates, 2,3,4,6-tetraiodobenzoates or mixtures thereof added to provide radiopacity.

Generally, the suggestions described above have involved combining a structural resin for the catheter with a second component, intended to affect the X-ray opacity, in a physical blend. Unfortunately, it has been discovered that such physical blends suffer from certain drawbacks. For example, the material blended in to add radiopacity often can be leached from the material. In extreme cases, the material can be leached from the catheter and absorbed systemically by the host.

In certain instances, as exemplified by the use of added barium sulfate, the incorporation of the added material has resulted in the creation of physical non-uniformities in the polymer blend causing the walls of the catheter to be abrasive. As a result, insertion and removal forces are increased which, in some cases, may result in patient discomfort.

The Goossens et al. patent referred to above, while not suggesting a mixture but instead suggesting a polymer having the properties of radiopacity and optical transparency, suffers from still other drawbacks. For example, it has been found that the Goossens et al. polymer exhibits stiffness which is not dissipated when a catheter made from this material is inserted into the blood vessel of a host.

SUMMARY OF THE INVENTION

This invention relates to polyurethanes, and to catheters and other articles formed from the polyurethanes, which are radiopaque due to the incorporation of halogenated moieties into the polymer structure. In preferred embodiments, the polyurethanes are additionally optically transparent. These unique polyurethanes can be produced by employing halogenated polyols, halogenated isocyanates, or both, as polymerization reactants.

Polyurethanes produced according to this invention retain the properties which have made polyurethanes particularly useful in the fabrication of medical devices, including catheters. Thus, they are biocompatible materials and materials which are known to soften at body temperatures. The polyurethanes can be thermoplastic polymers capable of being processed by conventional polymer techniques into shaped articles possessing outstanding mechanical properties including tensile strength, elongation at yield and flexural modulus.

Importantly, the polyurethanes of this invention are radiopaque because of structural units contained within the polymer itself. This eliminates the necessity to blend a material with the polymer to provide radiopacity. Thus, the disadvantage of physical blends are avoided. Because the radiopacity is obtained from halogenated moieties contained within the structure of the polymer, these moieties do not leach out during use of the catheter and do not create non-uniformities in the polymer blend.

In preferred embodiments, the polyurethanes are optically transparent in addition to being radiopaque. Polyurethanes which are radiopaque and yet optically transparent provide a unique combination of desirable properties for catheters in a polymer noted for its biocompatibility and other advantageous properties for medical applications.

BRIEF DESCRIPTION OF THE DRAWING

The invention will be further described with reference to the following description of preferred embodiments of the invention when considered together with the attached drawings, in which:

FIG. 1 is a perspective view of an intravenous catheter assembly illustrating a catheter according to the present invention;

FIG. 2 is a longitudinal cross-sectional view of the catheter assembly of FIG. 1.

DESCRIPTION OF PREFERRED EMBODIMENTS OF THE INVENTION

Figure 3:
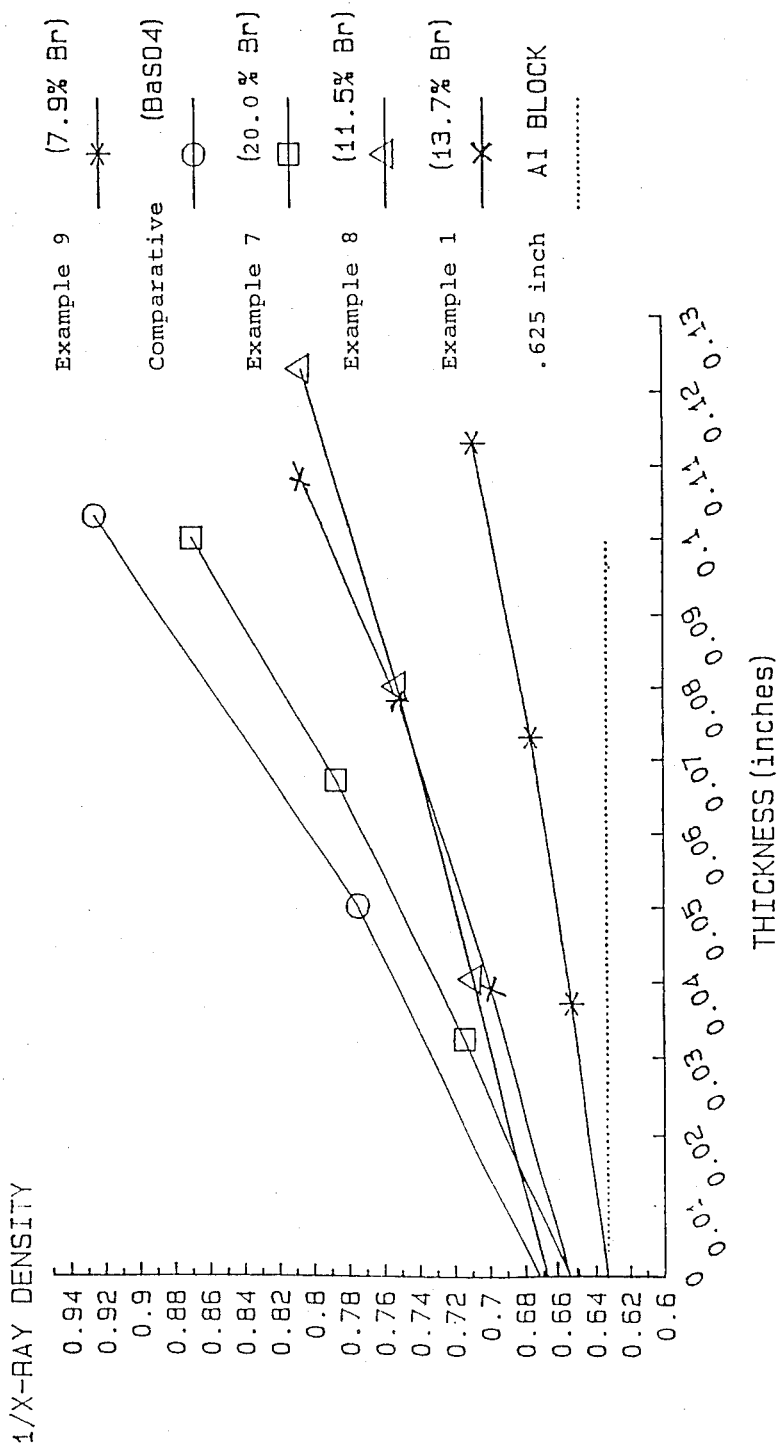
FIG. 3 is a comparative plot of the reciprocal of X-ray density vs. thickness for certain polyurethanes of this invention.

Referring to FIGS. 1 and 2, an intravenous catheter assembly is shown generally at 10. The assembly comprises an introducer needle 11 which is in the form of a hollow hypodermic needle having a point 12 on one end thereof. Needle 11 is secured at its blunt end to a plastic hub 13 which has a transparent blood-detecting chamber 14 integral with its proximal end. The entire hub and blood-detecting chamber assembly can be molded in one piece from a suitable clear plastic material. Needle 11 serves the function of introducing a flexible plastic catheter 15 into a vein or other body vessel. Catheter 15 is attached to a hub 16 at its proximal end and hub 16 is adapted to be removably secured to a fitting 17 on the distal end of hub 13.

The plug shown generally at 20 in the drawing includes an enlarged gripping surface 21, a tapered neck portion 22 for insertion into the proximal end of blood-detecting chamber 14 and a diaphragm 23 having a diametrically oriented slit 24 formed therein. Plug 20 can be molded in one piece with diaphragm 23 formed at the distal end of the plug from a relatively thin portion of the plastic material. Slit 24 can then be formed in the diaphragm by a cutting or other suitable procedure.

The size of slit 24 is not critical. However, it has been found to be desirable to form the slit in diaphragm 23 without the removal of any of the plastic material. This assures that air may be vented from the blood-detecting chamber but provides a seal against the passage of blood from the chamber. For purposes of illustration, slit 24 has been shown in the Figures in an enlarged condition so that it will be apparent that there is an opening in diaphragm 23.

To initiate the introduction of the needle 11 into a vein, the unit is fully assembled as shown in FIG. 2 with catheter 15 positioned over needle 11 and with plug 20 firmly seated within the proximal end of blood-detecting chamber 14. The introduction of the needle point 12 into a vein will cause blood to flow through the hollow needle and into blooddetecting chamber 14. Air contained within the hollow needle and the blood-detecting chamber will be forced by the blood through slit 24 in plug 20 out into the atmosphere. Blood flowing into chamber 14 can then be detected by the operator through the transparent wall of the chamber. Because of the extremely small size of slit 24, blood will be retained within the chamber and not permitted to pass through the axial opening in plug 20. When it is desired to attach an administration set or other device to the catheter hub, it is only necessary to withdraw the needle from the catheter and, thereby, expose the open female luer end of hub 16 for the appropriate male fitting.

Catheter 15 is formed from a polyurethane which is radiopaque, and preferably optically transparent. The preparation of such polyurethanes will now be described.

In general, polyurethanes are condensation products of reactions between diisocyanates (isocyanate compounds having a functionality of two) and polyols, such as diols. Polyurethane chemistry is well understood in the art. See, for example, Saunders, J. H. and Frisch, K. C., *Polyurethanes, Part I*, Interscience Publishers, New York (1962).

The diisocyanates can be aromatic or aliphatic. Examples of aromatic diisocyanates include toluene diisocyanate and diphenyl methylene diisocyanate. Examples of aliphatic diisocyanates include dicyclohexylmethane-4,4'-diisocyanate and isophorone diisocyanate.

Suitable polyols include low molecular weight diols, high molecular weight diols, and combinations thereof. Examples of low molecular weight diols include ethylene glycol, propylene glycol, butane diol, pentane diol, hexane diol, heptane diol and isomers of the same. Examples of high molecular weight diols include polyoxypropylene glycols, polytetramethylene glycols and polycarbonate glycols. The choice of low molecular weight diols, high molecular weight diols, or a combination, is usually dictated by a desire to obtain certain properties in the final polymer. Such properties include the degree of crystallinity, hardness, stiffness, and other properties.

The polyurethanes of this invention contain halogenated moieties in the polymer. A preferred method for producing such polyurethanes with halogenated moieties therein is to employ halogenated diols as a polymerization reactant.

Halogen-containing diols suitable for this invention include chlorine, bromine and iodinesubstituted low molecular weight aliphatic and aromatic glycols, polyester diols and polyether diols. Specific examples include mono-, di-, and tribromo neopentyl glycol; ester diols based on diethylene glycol, propylene glycol and tetrabromophthalic anhydride; and ethylene oxide adduct of tetrabromobisphenol-A. Similar chloro-, fluoro-, and iodo-glycols can also be used.

One commercially available halogenated diol is PHT4-Diol marketed by Great Lakes Chemical Corporation, West Lafayette, Ind. This compound is a diester of tetrabromophthalic anhydride and can be represented by the structural formula:

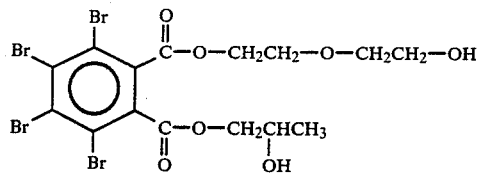

PHT4-Diol is a viscous, light tan colored liquid containing 46 percent aromatically bound bromine.

A similar compound is commercially available from Ethyl Corporation, Sayreville, N.J., under the name SAYTEX RB-79 DIOL. This is a mixed ester of tetrabromophthalic anhydride with diethylene glycol and propylene glycol.

Dibromoneopentyl glycol is another commercially available halogenated diol suitable for use with this invention. Dibromoneopentyl glycol is sold commercially by Dow Chemical, Midland, Mich., under the tradename FR 1138.

There are, of course, many additional commercially available halogenated diols. See, for example, Nametz, R. C., "Bromine Compounds For Flame Retarding Polymer Compositions, Part II: Thermosets," *Plastics Compounding*, September/October, 1984, pp. 54-66, the teachings of which are hereby incorporated by reference.

Another method for producing polyurethanes containing halogenated moieties according to this invention is to employ halogenated diisocyanate reactants in the polymerization reaction. Examples of suitable halogenated diisocyanates include dibromo diphenylmethane diisocyanate, tetrabromo diphenylmethane diisocyanate, dibromo dicyclohexylmethane diisocyanate and tetrabromo dicyclohexylmethane diisocyanate.

The halogen-containing polymerization reactants are employed in an amount which provides the final polyurethane with sufficient halogenated moieties to make the polymer radiopaque. The term "radiopaque" is used herein to mean that catheters and other shaped articles produced from the polyurethanes can be detected by customary X-ray examination procedures after insertion in a host.

Polymers containing at least 10 percent by weight of halogen in the polymer structure are preferred because of their outstanding radiopacity combined with the art-recognized physical, chemical and biological properties possessed by polyurethanes, particularly those properties which lend themselves to in vivo use of these materials. Higher amounts of halogenated moieties can be incorporated into the polyurethanes of this invention with the exact amount determined by the balance of properties desired.

In addition to possessing outstanding radiopacity, it has been found that the polyurethanes of this invention can also be optically transparent. Such materials are particularly preferred for use in catheters because of this unique combination of desirable properties. The term "optical transparency" is used herein to mean a material which, when formed into a catheter or other shaped article, will allow the presence of blood or other fluids to be visible from outside the catheter under normal lighting conditions. For example, a polyurethane is optically transparent if such a material, when formed into a tube having a wall thickness of about 0.01 inches or less, allows the passage of blood therein to be observed by the naked eye from outside the tube under normal lighting conditions.

Polyurethanes produced according to this invention can be thermoplastic or thermoset polymers. Thermoplastic polyurethanes are often preferred because they can be melt-processed by conventional polymer techniques, such as injection molding, extrusion, etc. Thermoplastic polyurethanes are essentially linear polymers having no significant cross-linking.

If thermoset materials are desired, the polyurethanes can be provided with cross-linking. One method for achieving such cross-linking is to employ reactants having functionalities of more than two. For example, triols can be employed as reactants to provide cross-linking.

Catalysts are generally employed to accelerate the polymerization of polyurethane reactants. Suitable catalysts include N-methyl morpholine, trimethylamine, triethylamine, zinc octoate, dibutyl tin dilaurate, dioctyl tin dilaurate and stannous octoate. Such catalysts are typically added to the polymerization reactants in small quantities, e.g., less than 1 percent by weight.

In addition to catalysts, other additives may be included in the polyurethane reaction mixture. These include, inter alia, processing aids, such as lubricants or waxes; ultra-violet or thermal stabilizers; fillers; colorants; etc.

One method for preparing the polyurethanes of this invention is known as the "one-shot" method. In the one-shot method, the hydroxyl-containing components, including any halogenated diols, the catalyst and other additives are combined and thoroughly blended into a premix. The diisocyanate is then combined with the premix, preferably stoichiometrically, under high shear agitation. A polymerization reaction ensues and the polymerization reaction can be monitored by monitoring the temperature profile of the mixture. The polymerization mixture can be poured into flat pans for cure, which are then placed into a convection oven and maintained at an elevated temperature until the cure is complete.

Alternately, the premixed components can be charged to one side of a typical two-component urethane processing machine, the diisocyanate charged to the other side, and the metering units adjusted to deliver the correct stoichiometric ratio to the mixing head. The correctly mixed material can be cast directly into flat pans for subsequent cure.

In yet another alternative polymerization, a prepolymer is formed by blending a portion of the diols with the isocyanates. Generally, this first portion is the high molecular weight diol or a blend of the high molecular weight and low molecular weight diols, including any halogenated diols. The prepolymer is then blended with the remaining diols to produce the polymerization product. This prepolymer technique is particularly advantageous with highly reactive diisocyanates, such as aromatic diisocyanates, and where the diol must be maintained at high temperature to maintain it in a liquid state.

In instances where reactants are solids at room temperature, these reactants can be heated to the melting point and then blended with the liquid components to provide liquid premixes. It is sometimes necessary to maintain these premixes at temperatures above ambient to insure that all ingredients remain in solution.

Catheters, according to the invention described herein, are useful in medical product applications. Such catheters can be used, for example, for arterial, intravenous and central line vascular catheters, cardiovascular catheters, such as balloon thermodilution catheters, balloon wedge pressure catheters, Berman and angiographic catheters and balloon pacing catheters. Tubing formed from the polyurethanes containing halogenated moieties according to this invention can additionally be employed in other in vivo applications, including enteral feeding. The polyurethanes of this invention can also be employed in additional applications wherein the unique combination of radiopacity and optical transparency is desired or required.

The invention is further illustrated by the following examples. All parts are by weight unless otherwise specified.

EXAMPLE 1

A premix of the following composition was formed at room temperature:

|  | Parts |
| --- | --- |
| Polytetramethylene ether glycol (M.W. ~ 1000): | 22.23 |
| 1,4-Butanediol: | 5.81 |
| Mixed ester of tetrabromophthalic anhydride with diethylene glycol and propylene glycol (46% Bromine): | 31.98 |
| Dioctyl tin dilaurate: | 0.03. |

39.95 parts of dicyclohexylmethane-4-4'-diisocyanate was subsequently added to the premix.

The reaction batch was mixed under high shear until the exotherm reached 60° C.; the batch was then cast into a 6"×6"×2" Teflon polytetrafluoethylene-coated pan and cured for 6 hours at 110° C. After cooling, a small block of the polymer cake was placed into a heated 6"×6"×0.030" aluminum mold, and compression molded into a clear, flat test plaque 0.030 inch thick. Test samples were taken from the plaque and certain properties of these samples were determined. The samples had a tensile strength of 4700 psi, an elongation at yield of 300%, a flexural modulus of 99,000 psi, and a Shore D scale hardness of 65. The polymer had a theoretical bromine content of 14.7%.

All samples were radiopaque and optically transparent.

EXAMPLE 2

Another polymer cake was prepared using the procedure of Example 1, except as follows.

The premix employed was:

|  | Parts |
| --- | --- |
| Polytetramethylene ether glycol (M.W. ~ 1000): | 27.28 |
| 1,4-Butanediol: | 3.70 |
| Mixed ester of tetrabromophthalic anhydride with diethylene glycol and propylene glycol (46% Bromine): | 32.11 |
| Dioctyl tin dilaurate: | 0.03. |

36.88 parts of dicyclohexylmethane-4-4'-diisocyanate was added to the premix.

A test plaque compression molded from this polymer had the following properties:
Tensile strength: 5300 psi
Elongation at yield: 150%
Flexural modulus: 86,000 psi
Shore D hardness: 71
Theoretical bromine content: 14.8%.

The test plaque was radiopaque and optically transparent.

EXAMPLE 3

A polymer cake was prepared using the procedure of Example 1, except as follows.

The premix employed was:

|  | Parts |
| --- | --- |
| Polytetramethylene ether glycol (M.W. ~ 1000): | 21.47 |
| 1,4-Butanediol: | 2.96 |
| Mixed ester of tetrabromophthalic anhydride with mixed glycols (43% bromine): | 36.98 |
| Dioctyl tin dilaurate: | 0.03. |

38.56 parts of dicyclohexylmethane-4,4'-diisocyanate was added to the premix.

The resulting polymer cake was compression molded into a test plaque which was not tested for certain physical properties because it was brittle. The hardness of the plaque was measured as 64 Shore D and the theoretical bromine content was calculated as 15.9%.

The plaque was radiopaque and optically transparent.

EXAMPLE 4

A polymer cake was prepared using the procedure of Example 1, except as follows. The brominecontaining diol was first melted into the polytetramethylene ether glycol to give a low viscosity liquid phase before reaction with the diisocyanate.

The premix employed was:

|  | Parts |
| --- | --- |
| Polytetramethylene ether glycol (M.W. ~ 1000): | 39.78 |
| Dibromoneopentyl glycol (61% bromine): | 24.33 |

|                        | Parts |
|------------------------|-------|
| Dioctyl tin dilaurate: | 0.03. |

35.86 parts of dicyclohexylmethane-4,4'-diisocyanate was added to the premix.

A test plaque compression molded from this polymer had the following properties:
Tensile strength: 7050 psi
Elongation at yield: 315%
Flexural modulus: 7000 psi
Shore D hardness: 64
Theoretical bromine content: 14.8%.

The plaque was radiopaque and optically transparent.

EXAMPLE 5

A polymer cake was prepared using the procedure of Example 4, except as follows.

The premix employed was:

|                                         | Parts |
|-----------------------------------------|-------|
| Polytetramethylene ether glycol (M.W.~2000): | 30.78 |
| Dibromoneopentyl glycol (61% bromine):  | 32.41 |
| Dioctyl tin dilaurate:                  | 0.03. |

36.78 parts of dicyclohexylmethane-4,4'-diisocyanate was added to the premix.

A test plaque compression molded from this polymer had the following properties:
Tensile strength: 5000 psi
Elongation at yield: 315%
Flexural modulus: 97,000 psi
Shore D hardness: 80
Theoretical bromine content: 19.8%.

The plaque was radiopaque and optically transparent.

Polymer cake was granulated into small particles, dried in a dessicant dryer and pelletized on a standard Berlyn 1½inch, 30:1 L/D extruder. The resin pellets were extruded into continuous lengths of hollow tubing having an internal diameter of approximately 0.033 inches and an outside diameter of approximately 0.049 inches as well as into continuous lengths of flat tape 0.02 inch thick. The pellets processed easily with consistent viscosity in the melt stage, tight dimensional control on the tubing and no build-up of polymer on the die face.

Properties obtained for the extruded tape were:
Tensile strength: 6000 psi
Elongation at yield: 400%.

Properties of the tubing were:
Flexural modulus: 115-145,000 psi
Radiopacity: comparable to polyurethane resin having 15-20% loading of BaSO$_4$.

In addition to being radiopaque, both the tubing and tape were optically transparent having a water-white color.

EXAMPLE 6

A polymer cake was prepared using the procedure of Example 4, except as follows.

The premix employed was:

|                                         | Parts |
|-----------------------------------------|-------|
| Polytetramethylene ether glycol (M.W.~2000): | 26.52 |
| Dibromoneopentyl glycol (61% bromine):  | 35.02 |
| Dioctyl tin dilaurate:                  | 0.03. |

38.43 parts of dicyclohexylmethane-4,4'-diisocyanate was added to the premix.

A test plaque compression molded from this polymer had the following properties:
Tensile strength: 4680 psi
Elongation at yield: 260%
Flexural modulus: 146,000 psi
Shore D hardness: 70
Theoretical bromine content: 21.3%.

The plaque was radiopaque and optically transparent.

EXAMPLE 7

A polymer cake was prepared using the procedure of Example 4, except as follows.

The premix employed was:

|                                         | Parts |
|-----------------------------------------|-------|
| Polytetramethylene ether glycol (M.W.~2900): | 31.20 |
| Dibromoneopentyl glycol (61% bromine):  | 32.85 |
| Dioctyl tin dilaurate:                  | 0.02. |

35.93 parts of dicyclohexylmethane-4,4'-diisocyanate was added to the premix.

A test plaque compression molded from this polymer had the following properties:
Tensile strength: 5000 psi
Elongation at yield: 300%
Flexural modulus: 96,000 psi
Shore D hardness: 70
Theoretical bromine content: 20.0%.

The plaque was radiopaque and optically transparent.

EXAMPLE 8

A polymer cake was prepared using the procedure of Example 4, except as follows.

The premix employed was:

|                                         | Parts |
|-----------------------------------------|-------|
| Polytetramethylene ether glycol (M.W.~1000): | 32.45 |
| 1,4-Butanediol:                         | 4.40  |
| Dibromoneopentyl glycol:                | 19.24 |
| Dioctyl tin dilaurate:                  | 0.03. |

43.88 parts of dicyclohexylmethane-4,4'-diisocyanate was added to the premix.

A test plaque compression molded from this polymer had the following properties:
Tensile strength: 4680 psi
Elongation at yield: 200%
Flexural modulus: 90,000 psi
Shore D hardness: 72
Theoretical bromine content: 11.5%.

The plaque was radiopaque and optically transparent.

EXAMPLE 9

|                                 | Parts |
|---------------------------------|-------|
| Polytetramethylene ether glycol | 43.23 |

-continued

| | Parts |
|---|---|
| (M.W. ~ 1000): | |
| 1,4-Butanediol: | 4.56 |
| Dibromoneopentyl glycol: | 13.21 |
| Dioctyl tin dilaurate: | 0.03. |

A test plaque compression molded from this polymer had the following properties:
Tensile strength: 6500 psi
Elongation at yield: 280%
Flexural modulus: 3,000 psi
Shore D hardness: 57
Theoretical bromine content: 7.9%.

The plaque was optically transparent but only marginally radiopaque.

EXAMPLE 10

A prepolymer was prepared with the following recipe:

| | Parts |
|---|---|
| Polytetramethylene ether glycol (M.W. ~ 2000): | 31.58 |
| Dibromoneopentyl glycol: | 14.27 |
| Dioctyl tin dilaurate catalyst: | 0.01 |
| p,p'-Diphenylmethane diisocyanate | 35.16. |

The polytetramethylene ether glycol and p, p'-diphenylmethane diisocyanate were added to a glass reactor and heated to approximately 100° C. under agitation. The mixture was maintained at 100° C. for one hour, then the dibromoneopentyl glycol and half the amount of catalyst was added. The mixture exothermed to 120°–130° C., and was held at that temperature for 2 hours. After cooling to 100° C., an additional 18.98 parts by weight dibromoneopentyl glycol and the remaining catalyst were added. The mixture was agitated for an additional 3 minutes, then poured immediately into a 6"×6"×2" Teflon polytetrafluoro-ethylene-coated pan and cured for 4 hours at 150° C. After cooling, the polymer cake was granulated into small particles, dried in a dessicant drier, and pelletized on a small extruder/chopper. The pellets were extruded into continuous lengths of hollow tubing.

The polymer produced from this example has a bromine content of 19.9% by weight.

The tubing produced was radiopaque and optically transparent.

EXAMPLE 11

A polymer was prepared using the same procedure as in Example 10, except as follows.
The recipe employed was:

| | Parts |
|---|---|
| Polytetramethylene ether glycol (M.W. ~ 1000): | 41.17 |
| Dibromoneopentyl glycol: | 7.26 |
| Dioctyl tin dilaurate catalyst: | 0.01 |
| p,p'-Diphenylmethane diisocyanate | 34.00. |

After completing the prepolymer reaction, an additional 17.56 parts by weight dibromoneopentyl glycol and remaining catalyst were added to extend the prepolymer. This mixture was agitated for an additional 3 minutes and cast immediately into a Teflon coated pan and cured for 4 hours at 150° C. The identical work-up procedure to Example 10 was followed to give a polymer resin containing 15.1% bromine. Tubing extruded from the resin was radiopaque and optically transparent.

EXAMPLE 12

The X-ray opacity for some of the polyurethanes described in the aforementioned Examples was determined, as follows. Strips were cut from compression molded polymer plaques. The individual plaques varied in thickness between 0.030 inch and 0.040 inch. The specific dimensions of each plaque are given by the lowest measured dimension for each example shown in the table below. The strips were stacked to various thicknesses, as shown in the table, for X-ray opacity measurements. The samples were then placed under a ⅜" thick block of aluminum 1100 (99% pure) and X-rays were taken. The equipment and conditions were:

X-ray machine - G.E. Sentry 3, 12 pulse
Film - Kodak AGFA Gevaert
Machine settings - 35 inch focal distance
1 MAS (200 MA) (.005 sec)
66 KVp.

The image of each sample was then measured on the film using a densitometer. The sample density is the densitometer reading of the sample plus the film fog value. Film fog is the densitometer reading on an area of the negative not exposed to X-ray. The reciprocal of the sample density, a measure of radiopacity, was plotted against sample thickness. The values for zero thickness are extrapolated values. The data obtained are shown below:

| Sample | Bromine Content % | Thickness (in) | 1/X-Ray Density |
|---|---|---|---|
| Example 9 | 7.9 | .113 | .709 |
| " | 7.9 | .073 | .676 |
| " | 7.9 | .037 | .653 |
| " | 7.9 | 0 | .633 |
| Example 8 | 11.5 | .123 | .806 |
| " | 11.5 | .08 | .752 |
| " | 11.5 | .04 | .709 |
| " | 11.5 | 0 | .667 |
| Example 1 | 14.7 | .108 | .806 |
| " | 14.7 | .078 | .752 |
| " | 14.7 | .039 | .699 |
| " | 14.7 | 0 | .654 |
| Example 7 | 20.0 | .1 | .87 |
| " | 20.0 | .067 | .787 |
| " | 20.0 | .032 | .714 |
| " | 20.0 | 0 | .654 |
| (BaSO4) | — | .103 | .926 |
| (BaSO4) | — | .05 | .775 |
| (BaSO4) | — | 0 | .671 |
| Aluminum Block | — | .625 | .633. |

The polyurethanes incorporating BaSO4 were employed for comparative purposes. These samples were prepared as follows. The base polyurethane resin was Pellethane 2363 (Dow Chemical) in pellet form. This material was melt blended with 19.7 percent of BaSO4 in a Warner Pfleiderer ZSK 30 twin screw compounder to produce extruded strands. The strands were chopped into pellets which then had BaSO4 uniformly dispersed throughout. These pellets were then compression molded into a plaque with thickness of 0.05 inch.

The data set forth in the table above is plotted in FIG. 3. This data indicates that it is preferable to employ at least about 10%, by weight, halogen in the polyurethane structure because of the outstanding x-ray opacity obtained above this amount.

In view of the teachings herein, those skilled in the art will recognize, or will be able to develop using no more than routine experimentation, many equivalents to the specific embodiments of the invention described herein. Such equivalents are intended to be encompassed by the following claims.

What is claimed is:

1. A catheter formed from a polyurethane containing sufficient halogenated moieties in the polymer structure to make the catheter radiopaque.

2. A catheter of claim 1 wherein said polyurethane contains at least 10 weight percent halogen.

3. A catheter of claim 2 wherein said polyurethane contains said halogenated moieties in its backbone.

4. A catheter of claim 3 wherein said halogenated backbone includes a halogenated diol.

5. A catheter of claim 4 wherein said halogenated diol comprises a brominated diol.

6. A catheter of claim 5 wherein said brominated diol comprises a mixed ester of tetrabromophthalic anhydride with diethylene glycol and propylene glycol.

7. A catheter of claim 5 wherein said brominated diol comprises dibromoneopentyl glycol.

8. A catheter of claim 3 wherein said backbone includes a halogenated diisocyanate.

9. A catheter of claim 3 wherein said backbone includes a halogenated diol and a halogenated diisocyanate.

10. A catheter of claim 1 which is optically transparent.

11. A catheter of claim 3 which is optically transparent.

12. A catheter of claim 5 which is optically transparent.

13. A polyurethane containing sufficient halogenated moieties in the polymer structure to make the polyurethane radiopaque.

14. A polyurethane of claim 13 wherein said halogenated moieties are contained in the polymer backbone.

15. A polyurethane of claim 14 containing at least about 10 weight percent halogen in the polymer structure.

16. A polyurethane of claim 15 wherein said halogenated backbone moieties are formed from a halogenated diol.

17. A polyurethane of claim 16 wherein said halogenated diol comprises a brominated diol.

18. A polyurethane of claim 17 wherein said brominated diol comprises a mixed ester of tetrabromophthalic anhydride with diethylene glycol and propylene glycol.

19. A polyurethane of claim 17 wherein said brominated diol comprises dibromoneopentyl glycol.

20. A polyurethane of claim 15 wherein said backbone includes a halogenated diisocyanate.

21. A polyurethane of claim 13 which is optically transparent.

22. A polyurethane of claim 17 which is optically transparent.

23. A radiopaque polyurethane comprising the reaction product of:
    (a) a diisocyanate; and
    (b) a diol selected from the group of low molecular weight diols, high molecular diols, or a combination of both;
at least one of said diisocyanate and said diol being halogenated and present in a sufficient quantity to make said polyurethane reaction product radiopaque.

24. A polyurethane of claim 23 wherein said diol includes an amount of a brominated diol sufficient to provide said polyurethane with at least about 10 weight percent bromine therein.

25. A shaped article formed from a polyurethane containing sufficient halogenated moieties in the polymer structure to make the shaped article radiopaque.

26. A radiopaque optically-transparent chateter formed from a polyurethane comprising a reaction product of a brominated diol and a diisocyanate, said polyurethane containing at least about 10 weight percent bromine in its backbone.

* * * * *